(12) United States Patent
Little et al.

(10) Patent No.: US 6,462,334 B1
(45) Date of Patent: Oct. 8, 2002

(54) ANALYTICAL METHOD AND APPARATUS

(75) Inventors: Christopher John Little, Datchet;
Raymond Peter William Scott,
Seddlescombe; **John Michael Devereux
De La Pena**, Banbury, all of (GB)

(73) Assignee: Scientific Detectors Limited (GB)

( * ) Notice: Subject to any disclaimer, the term of this patent is extended or adjusted under 35 U.S.C. 154(b) by 0 days.

(21) Appl. No.: 09/581,467

(22) PCT Filed: Dec. 10, 1998

(86) PCT No.: PCT/GB98/03672

§ 371 (c)(1),
(2), (4) Date: Aug. 7, 2000

(87) PCT Pub. No.: WO99/31481

PCT Pub. Date: Jun. 24, 1999

(30) Foreign Application Priority Data

Dec. 12, 1997  (GB) ............................................... 9726199

(51) Int. Cl.⁷ .......................... H01J 49/00; G01N 35/00
(52) U.S. Cl. ....................... 250/281; 250/282; 250/288; 73/864.81
(58) Field of Search ................................ 250/281, 288, 250/282; 73/61.52, 864.81; 210/198.2, 198.3

(56) References Cited

U.S. PATENT DOCUMENTS

| 3,128,619 | A | * | 4/1964 | Liberman ................... 73/61.1 |
| 3,566,677 | A | * | 3/1971 | Cole .......................... 73/61.5 |
| 4,178,507 | A |   | 12/1979 | Brunnee |
| 4,740,298 | A | * | 4/1988 | Andresen et al. ........ 210/198.2 |
| 5,698,358 | A | * | 12/1997 | Yu .............................. 156/157 |
| 6,132,685 | A | * | 10/2000 | Kercso et al. ............. 422/104 |

FOREIGN PATENT DOCUMENTS

DE    2732746    3/1979

* cited by examiner

Primary Examiner—Jack Berman
Assistant Examiner—Kalimah Fernandez
(74) Attorney, Agent, or Firm—Kilpatrick Stockton LLP

(57) ABSTRACT

The invention provides an analytical apparatus comprising: (i) supply means (14) for supplying a sample (30) to be analysed; (ii) analysing means (32, 36) for analysing at least one property of the sample (30) to be analysed; and (iii) conveying means (16) for conveying the sample (30) between the supply means (14) and the analysing means (32, 36) wherein the conveying means (16) comprises an oxidized surface (18) layer which receives the sample (30). Preferably the conveying means (16) is a wire or tape, such as titanium.

21 Claims, 6 Drawing Sheets

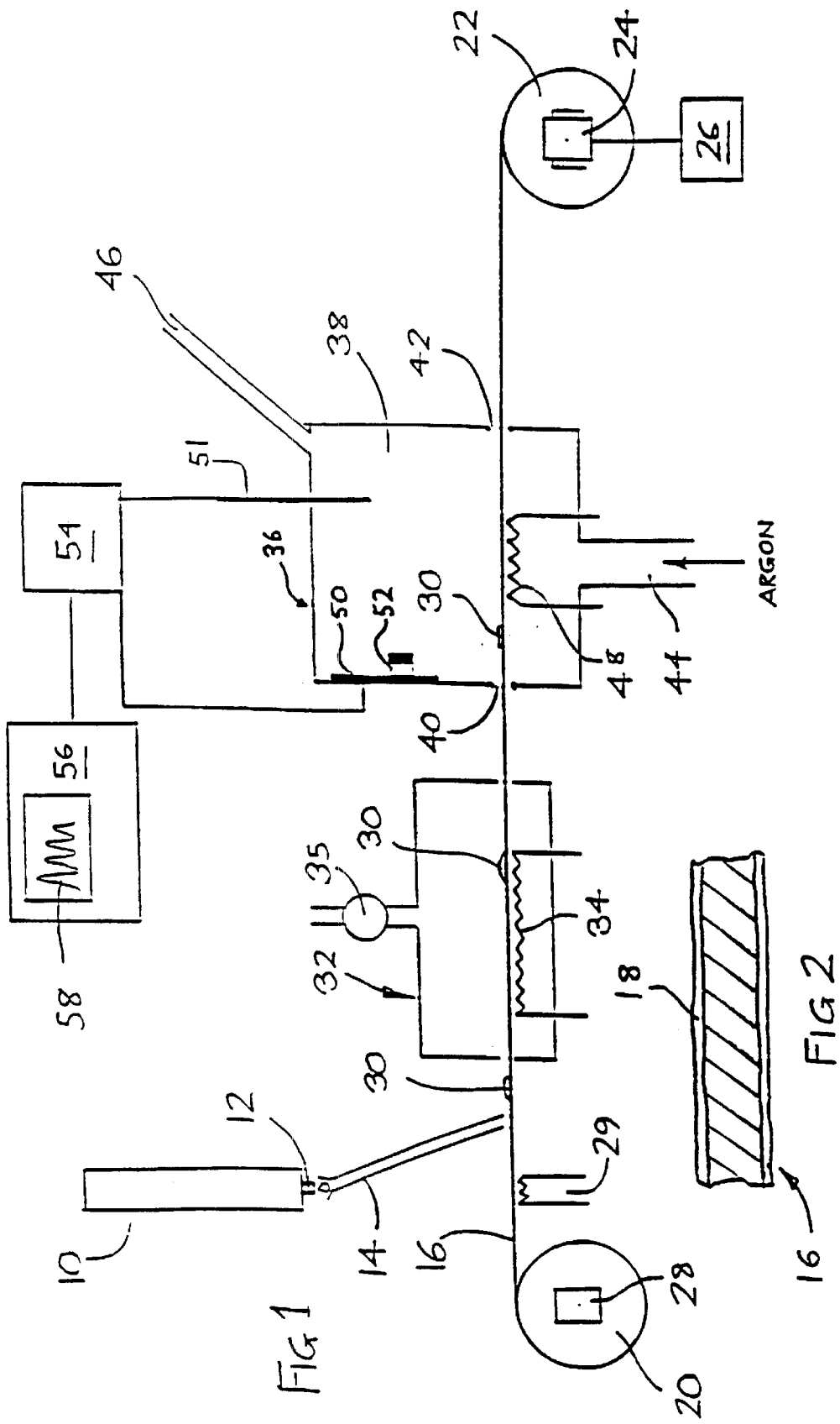

ANALYTICAL METHOD AND APPARATUS

The invention relates to a method of and apparatus for analysing a sample, and particularly to those comprising the use of conveying means to convey a sample to an analyser.

For many years it has been known to provide a chromatography column for separating liquid mixtures containing various components dissolved or dispersed therein. During the chromatographic process, the individual components are separated by a known process using apparatus comprising a mobile phase supply, a sampling device, a column and a detector, such as HPLC, gel permeation chromatography, or ion exchange chromatography enabling the quantity and nature of each component to be determined. Hitherto, different methods of detection have been proposed.

In one method, UV detection has been found to be highly sensitive, accurate and simple to use. However, one major limitation is that for UV detection to be effective, the compound to be analysed must absorb UV. This means that the technique cannot be used for several major classes of compounds, including carbohydrates, alcohols, detergents and aliphatic hydrocarbons. Also solvent choice is limited to U.V. transparent solvents.

In another method, refractive index detection is used. Whilst it is a widely used method, it is less sensitive than the UV method described above and tends to be subject to considerable instability arising from eluent changes. It cannot be used with what is known in the art as Gradient Elution techniques.

In a further method, the components separated by chromatography are transported on a wire to a furnace where they are heated and pyrolysed. The pyrolysis products then pass by means of a complex set of conduits into an argon detector and are detected. In another embodiment the solute on the wire is burnt to carbon dioxide which is sucked into a hydrogen stream that passes over a nickel catalyst. The nickel catalyst converts the carbon dioxide quantitatively to methane which is detected by a flame ionisation detector (FID). The disadvantage of these processes is the need for a complex set of conduits and the dilution of the pyrolysis or oxidation product during the process. As the argon detector is concentration sensitive the dilution of pyrolysis produced in the carrier argon stream reduces the sensitivity. As the FID is mass sensitive and not concentration sensitive dilution is not important but the dispersion of the peak in the conduit (peak broadening) and the high noise generated by the catalytic conversion significantly reduces the sensitivity.

An object of the present invention is to provide improved methods and apparatus for detecting components of a mixture which may have been separated by chromatography.

According to a first aspect of the invention there is provided an analytical apparatus comprising:
  (i) supply means for supplying a sample to be analysed;
  (ii) analysing means for analysing at least one property of the sample to be analysed; and
  (iii) conveying means operable to convey the sample between the supply means and the analysing means, wherein the conveying means comprises an oxidised surface layer which receives the sample.

The property may be a physical property, such as viscosity or melting temperature, of the sample or a chemical property, such as the chemical composition of the sample.

The sample may be components of a mixture which has been previously separated by chromatography.

The anlaysing means may be an analysing chamber, preferably without the need for conversion steps known hitherto.

Preferably the oxidised surface layer is in the form of a continuous surface film. The oxidised surface layer may be porous. The oxidised surface layer is preferably readily wettable by solvents, especially aqueous and non-aqueous solvents such as water and polar solvents. Examples of polar solvents include alcohols, such as ethanol and propanol, and DMSO. Preferably the oxidised surface layer is readily wettable by hydrocarbons including aromatic and non-aromatic, substituted and non-substituted alkyls.

Preferably the sample is applied to the conveying means without substantial diffusion along the conveying means.

The conveying means may comprise a metal, the metal having an oxidised surface layer.

Preferably, the conveying means is a wire which has an oxidised surface layer.

Alternatively a tape of material or a disk of material may be used instead of the wire. The latter two forms of conveyor have an oxidised surface layer, and are less likely to break than wire. Tape is especially preferred. A typical width of tape is 1.5 mm, with a thickness of 0.1 mm.

In that respect, and according to a second aspect of the invention, there is provided a method of detecting components of a mixture which have been separated by chromatography comprising the steps of providing a conveyor, such as a metal wire or tape, which has an oxidised surface layer, depositing sequentially on the oxidised surface layer the separated components of the mixture, and moving the wire and each component thereon to detection apparatus where analysis of each sample takes place.

Preferably, the conveying means, such as wire or tape, is made of titanium and the layer is oxidised titanium. The oxidised titanium forms a continuous porous surface film on the titanium metal and greatly enhances the carrying capabilities of the wire or tape. The oxidised wire wets very easily and will carry without difficulty both aqueous and non-aqueous liquids. Preoxidised titanium wire comprising an oxidised surface coating is commercially available, for example from Alloy Wire International, Cradley Heath, West Midlands, United Kingdom.

Other suitable metals comprising an oxidised surface layer include molybdenum, aluminium, iron, palladium and platinum.

The conveying means such as wire or tape is preferably carried on a supply spool and the invention may include drawing off the wire from the supply spool by means of a take up spool. A motor, such as a stepper motor, may be computer controlled to draw the wire or tape at a desired rate from the supply spool. The invention preferably includes controlling the tension of the wire between the spools to maintain a substantially constant tension in the wire particularly when the wire is heated as set out below.

A traverse mechanism may be provided to ensure that, for example, the tape/wire is regularly wound across the take up spool.

Alternatively the conveying means may be moved by means of one or more rollers in contact with the conveying means. This has the advantage that the speed of the conveying means does not vary according to the amount of e.g. tape/wire on the take up spool.

Preferably, the apparatus of the invention comprises an analyser chamber.

In a preferred embodiment the inventors have found that where a conveying means, such as tape or wire, is used according to the first or second aspect of the invention, wetting of the tape or wire with the separated components of the mixture can be improved by providing a polar cone opposite an aperture supplying the separated components of the mixture.

The separated components of the mixture may be supplied to the surface of the tape or wire from an aperture in, for example, the end of a supply tube the end of which may be cone-shaped. The cone, such as a titanium cone, comprising an oxidised surface coating, may be provided on the opposite side of the tape or wire with the tip of the cone directed towards the aperture. The cone draws off surplus mixture by directing the surplus mixture away from the tip of the cone, down the sides of the cone, to collection means. The oxidised layer on the surface of the cone improves the wettability of the cone and improves the ability of the cone to direct surplus mixture away from the wire or tape, thus preventing diffusion of the separated components along the wire or tape. Titanium is especially preferred as the material for the cone.

The aperture and cone may be positioned so that a continuous stream of separated components joins the aperture to the cone, with the wire or tape passing through the stream.

A strongly dispersive coating may be provided each side of the aperture providing the separated components. This prevents build up, by evaporation, of contaminants, which would ultimately contaminate the separated components, causing random noise. PTFE is especially preferred as the coating. This may be used in combination with the cone, described above.

The conveyor, such as wire or tape, may be subjected to heat prior to entry into the detection apparatus or analyser chamber to vaporise solvent from the component on the conveyor or wire.

Alternatively a nebuliser may be used to spray the sample onto the conveying means. Preferably the nebuliser is a heated nebuliser.

The distance between the nebuliser and the surface of the conveying means may be adjusted so that at least some of any solvent with the sample evaporates before the sample contacts the surface of the conveying means. This allows the amount of diffusion of the sample on the conveying means to be controlled.

Preferably the nebuliser comprises an inner tube through which the sample is passed, an outer tube through which a gas, such as air, is passed, and a nozzle where the gas and sample are combined and through which they are propelled. The outer tube may comprise heating means for preheating the gas and sample stream.

Means for making the mixing of the gas and sample turbulent, thus improving the mixing, may be provided. Such means include vanes for causing the gas to rotate prior to, or after, leaving the nozzle. Alternatively, the outside of the inner tube may be shaped, e.g. in the form of a helix, to rotate the gas flow.

In either aspect of the invention or in any of the consistory clauses relating thereto, the component on the conveyor or wire may be subjected to pyrolysis to convert the component to a gas or sol such as smoke, the pyrolysis preferably taking place within or adjacent to the analyser chamber itself. The pyrolysis may be effected by heating coils disposed adjacent the conveyor or wire or by induction heating or by other means such as laser heating.

The analyser chamber may be defined in a housing formed from a machineable glass or ceramic or from PTFE or PEEK (polyether ether ketone), or from a metal such as stainless steel, copper or brass.

Preferably, one or more gas chromatography detectors such as argon ionisation detectors, are used to detect the pyrolysed components given off by heating. Argon ionisation detectors are discussed in detail in the work by Scott R. P. W. et al, Chromatographic Detectors, Chromatographic Science Series, Vol.73, Marcel Dekker Inc. (New York), pages 119–147 (1996).

In noble gases, such as argon, the outer octet of electrons is complete and as a consequence, collisions between argon atoms and electrons resulting from an ionisation source are perfectly elastic. Consequently, if a high potential is set up between two electrodes in argon, and ionisation is initiated by a suitable radioactive source, electrons will be accelerated toward the anode and will not be impeded by collisions with argon. However, if the potential of the anode is great enough, the electrons will have sufficient kinetic energy that on collision with an argon atom energy can be absorbed and a metastable atom can be produced. The metastable argon atom carries no charge but has an electron displaced to an outer orbit. This gives the metastable atom sufficient energy (ca. 11.6 eV) to ionise most organic molecules. Upon collision with an organic molecule the electron in the outer orbit collapses back to its original orbit, followed by expulsion of an electron from the organic molecule. The electrons produced by this process are collected at the anode, resulting in a large increase in anode current which is measured.

Accordingly the analyser chamber is preferably provided with a source of a noble gas, such as argon, an anode, a cathode, a potential between anode and cathode, and a radioactive source. The radioactive source may be an alpha-particle emitter, such as Americium, or a beta-particle emitter, such as $Ni^{63}$. This form of sensor is very sensitive, and is universal in its response and does not have the sensitivity difficulties associated with using different solvents with other forms of sensor. A change in current flowing between the electrodes indicates the presence of separated components within the analysis chamber. This may be recorded for example graphically or on a computer.

Other inert gases, such as helium, neon or krypton, or a mixture thereof, may be used instead of argon.

If desired, the invention may include providing further means for analysis downstream of the analyser chamber. The method of the invention is particularly advantageous in that respect as the pyrolysed sample is not further destroyed in the analyser chamber and can be passed for further analysis after the initial analysis has been completed. The further analysis may be performed by detectors such as Electron Capture, Phosphorous and Sulphur selective detectors, Atomic Absorption Spectroscopy and Time of Flight mass spectrometry.

The argon ionisation detector may be omitted and one or more of the other detectors described above may be used instead.

The provision of an electron capture detector downstream of a argon gas detector is especially preferred. Such detectors are discussed in the book by Scott R. P. W. (Supra). Such detectors operate on a different principle from that of argon detecotrs. A low energy $\beta$-ray source, such as $Ni^{63}$ is used to produce electrons as ions. Sensors can be made to function in a D.C. mode with a constant current applied across the sensor electrodes, or as pulsed mode, in which a pulsed potential is used.

In the D.C. mode, a constant electrode potential of a few volts is employed that is just sufficient to collect all the electrons that are produced and provide a small standing current. If an electron capturing molecule (for example a molecule containing a halogen atom with seven electrons in its outer shell) enters the sensor, the electrons are captured by the molecule and become charged. The mobility of the captured electrons are much reduced compared with free electrons and, furthermore, are likely to be neutralised by collision with any positive ions that are also generated. As a consquence, the electrode current falls dramatically.

In pulsed mode, a mixture of machine in argon is usually used as the carrier gas. The "off period" of the potential allows electrons to re-establish equilibrium with the gas resulting in improved sensitivity.

Electron-capture detectors are extremely sensitive and are widely used in the analysis of halogenated compounds. Thus the preferred combination of an argon detector with an electron capture detector combines the universality of the argon detector with the specificity of the electron-capture detector in the same apparatus. The electron capture detector may be placed immediately downstream of the argon detector.

The inventors have found that some samples, after having been pyrolysed, appear to be charged, thus reducing the sensitivity of, for example, the argon detector. Accordingly, means to neutralise the charge on the pyrolysed sample may be provided. This may be, for example, provided by means of an electron capture detector, for example, before the argon detector.

The inventors have found that pyrolysis is less suitable for some highly oxygenated compounds, such as sugars, which do not pyrolyse completely, but instead tend to form residues which remain on the conveyor. The high temperature which is required to completely pyrolyse such residues can ionise the pyrolysed compounds, resulting in difficulty in accurately detecting the compounds in, for example, argon detectors.

According to a further aspect of the invention there is provided a method of detecting components of a mixture separated by chromatography, comprising the step of, depositing sequentially on a conveyor the separated components of the mixture, and moving the conveyor and each compound thereon into an analyser chamber in which analysis of each sample takes place; wherein the analysis chabmer is an argon detector comprising a source of noble gas, such as argon, an anode, a cathode, a potential between the anode and cathode, and a radioactive source.

The conveyor, method of supplying the separated components onto the conveyor, and the chamber housng may be as defined previously for the first and second aspects of the invention. Preferably the radioactive source is an alpha-particle emitter, such as Americium, or a beta-particle emitter such as $Ni^{63}$.

In this preferred embodiment the separated components react with metastable argon in situ. The electrons emitted by the separated components are detected by the increase in current at the anode, as discussed previously.

The argon gas, once it has passed through the chamber, may be directed to an electron capture detector, and/or other detectors as discussed previously, for further analysis.

According to a further aspect of the invention there is provided apparatus for carrying out the methods according to the invention and in accordance with any of the consistory clauses related thereto.

One difficulty experienced by the inventors has been sealing the aparatus. The detectors used are extremely sensitive, hence, if the apparatus is not properly sealed, false readings may be produced from components in the surrounding atmosphere. Conventional seals of rubber, ceramic or metal surrounding the conveyor rapidly wear out, owing to the abrasive nature of the conveyor. The inventors have therefore developed an improved seal.

Accordingly, a still further aspect of the invention provides a seal for an aperture comprising a plurality of magnetisable particles maintained in a sealing position by one or more magnet means. The seal may be for use with a conveyor which moves through it.

The magnetisable particles may be iron, iron coated with latex, or other commercially available magnetisable particles. The magnetisable particles are maintained in a sealing position by, for example, one or more iron or ceramic magnets or electro magnets. The magnetic field from the or each magnet keeps the magnetisable particles in a sealing position such as in the form of a "slug" of particles through which th conveyor passes. Preferably the particles are selected so that if any do escape into the analyser chamber (s), they are not detected or do not interfere with the analysis.

Another aspect of the invention provides a seal for an aperture comprising magnetic particles capable of being maintained in a sealing position by one or more magnet means.

A method and apparatus in accordance with the invention will now be described by way of example, with reference to the accompanying drawings, in which:

FIG. 1 is a diagrammatic representation of apparatus in accordance with the invention for detecting components of a mixture separated by chromatography;

FIG. 2 is a diagrammatic cross-section through a section of wire used to transport the components separated by chromatograhy;

Figure 3:
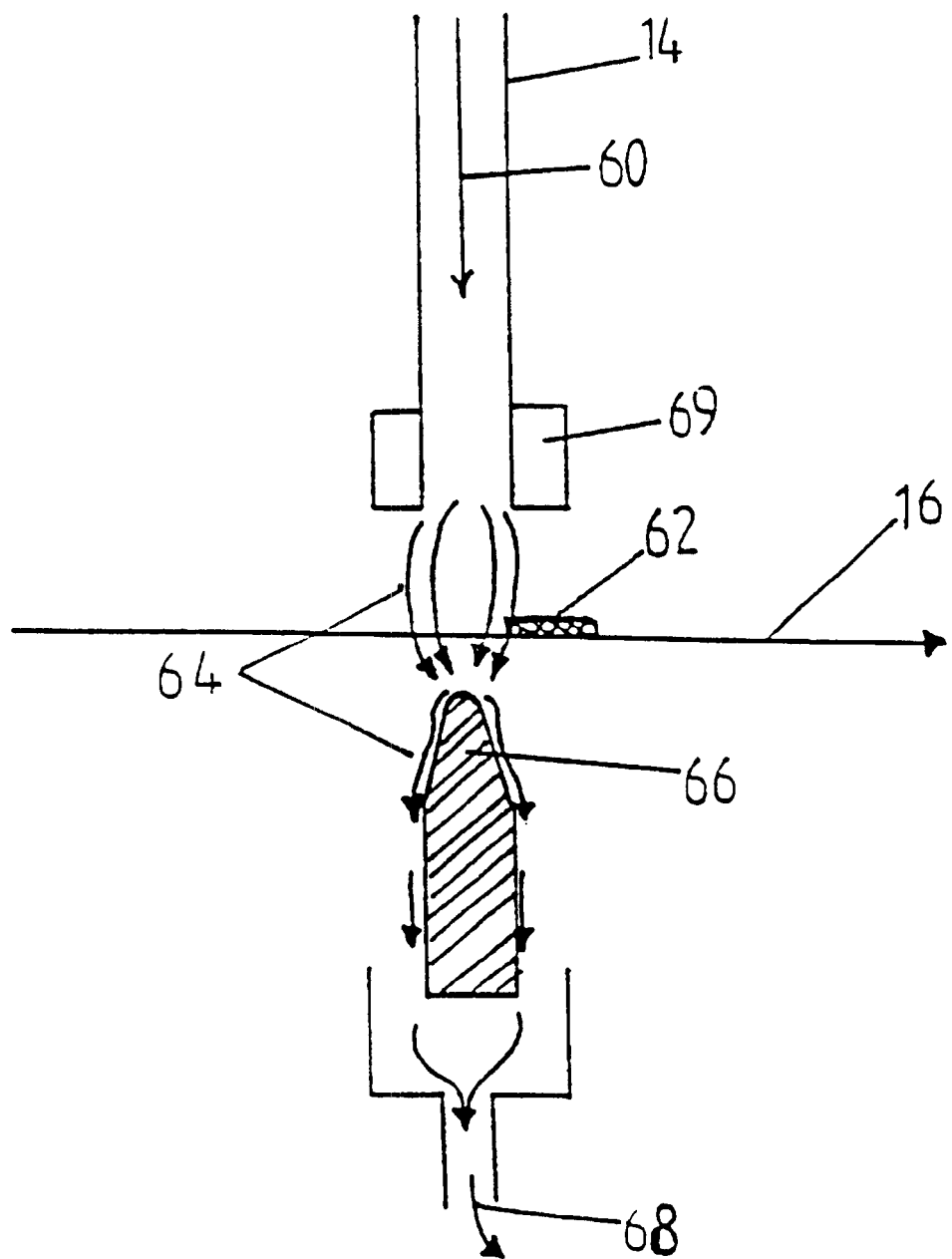
FIG. 3 shows a detail of the wetting device for applying sample to a wire.

Looking at FIG. 1, a chromatography column 10 of known kind has its outlet 12 arranged adjacent the upper end of a feeder pipe 14. The feeder pipe 14 receives solvent from the chromatography column 10 containing a component separated from other components in the chromatography column 10. The lower end of the feeder pipe 14 is arranged immediately above a conveyor wire 16. The conveyor wire 16 is an oxidised titanium wire, the oxide forming a surface layer 18 as shown in FIG. 2. The wire 16 is wound on a supply spool 20 and the wire is drawn from the spool 20 through the apparatus by means of a take-up spool 22. The take-up spool 22 is driven by a stepper motor 24 under the control of a computer 26.

As the wire 16 is drawn through the apparatus, samples 30 of the separated components from the chromatography column are deposited sequentially at spaced-apart intervals on the wire 16. A device (not shown) may be provided for maintaining a constant tension in the wire 16. A heater 29 is arranged immediately downstream of the spool 20 which effectively oxidises and cleans the wire 16 before it reaches the outlet of the feeder piper 14.

From the outlet end of the feeder pipe 14, the deposited component samples 30 enter an evaporation station 32 where a heating device 34 such as heating coil or induction heating device is arranged. Solvent containing the separated components is evaporated at the evaporation station 32 to leave the component on the wire 16. A pump 35 is used to reduce the pressure the evaporation station 32 for drawing off the solvent vapour.

From the evaporation station 32, the wire passes through a detection unit 36 which defines an analyser chamber 38.

The detection unit 36 is made, for example, from machineable glass or ceramic or from other suitable materials such as PTFE or PEEK.

The detection unit 36 forms a housing having entry and exit ports 40, 42 for the wire 16, an inlet 44 for argon gas and an outlet 46. A heating device 48 such as a heating coil or an induction heating device is arranged in the chamber 38 immediately adjacent the wire 16. The detection unit housing carries electrodes 50, 51 and also carries a radioactive substance such as Americium which has an intrinsically safe level of radiation and which is readily available from a domestic smoke detector. The Americium 52 emits α particles into the chamber 38. Alternatively Nickel-63 can be used as a β-emitter.

As a sample 30 is moved into the chamber 38, the heating device 48 pyrolyses the sample 30 converting it to pyrolysis products within the chamber 38. The pyrolysis products mixes with the argon gas fed through the inlet 44, the argon being introduced at a pressure slightly higher than atmospheric pressure to exclude ambient air from entering the chamber 38 through the entry and exit ports 40,42. A typical flow rate of Argon of up to 50 ml/min, preferably 15–20 ml/min. is used. The detector unit 36 operates as described earlier to detect the pyrolysed components of sample 30 carried into the chamber 38 by the wire 16. The electrodes 50,51 of the detector are arranged in a detection circuit indicated generally at 54.

The gas flow stream leaves the chamber 38 through the exit 46 and, from there, can be directed to further detectors if desired. The detection circuitry 54 responds to current flow between the electrodes 50,51 and provides an output signal to a visual display 56. The dispaly 56 may produce a graphical representation 58 of the relative quantities of the vrious componnets of a substance passing through the chromatography column. It has been found that the method of detection is particularly sensitive bearing in mind that the component sample 30 passes through only a single converson step for measurement purposes, the conversion step taking place within the analyser chamber 38 itself. Moreover, the pyrolysed component when mixed with the argon can be tested again after it leaves outlet 46 by other detectors. It is also possible to use a single inert gas in the anlayser chamber.

FIG. 3 shows a preferred arrangement of the feeder pipe 14 which supplies solvent from chromatograhy column 10. Pipe 14 delivers solvent containing the separated components in the direction of arrow 60. Preferably the pipe 14 is made of stainless steel. The solvent flows over wire 16 and forms a film 62. Excess solvent is directed away from the end of pipe 14 in the direction of flow lines 64 by the surface oxidised titanium cone 66. The oxidised surface of the cone 66 has been found to draw the excess solvent away efficiently, and to allow it to be drained off as a waste 68. This produces improved distribution of solvent on the wire 16, with less diffusion of the film 62 than conventional systems.

When the solvent is a hydrophilic (polar) solvent, further improvement can be achieved by placing a hydrophobic (dispersive) mateial, such as PTFE around the end 69 of the pipe 15. This produces a cleaner separation of the solvent from the end of the pipe.

Figure 4:
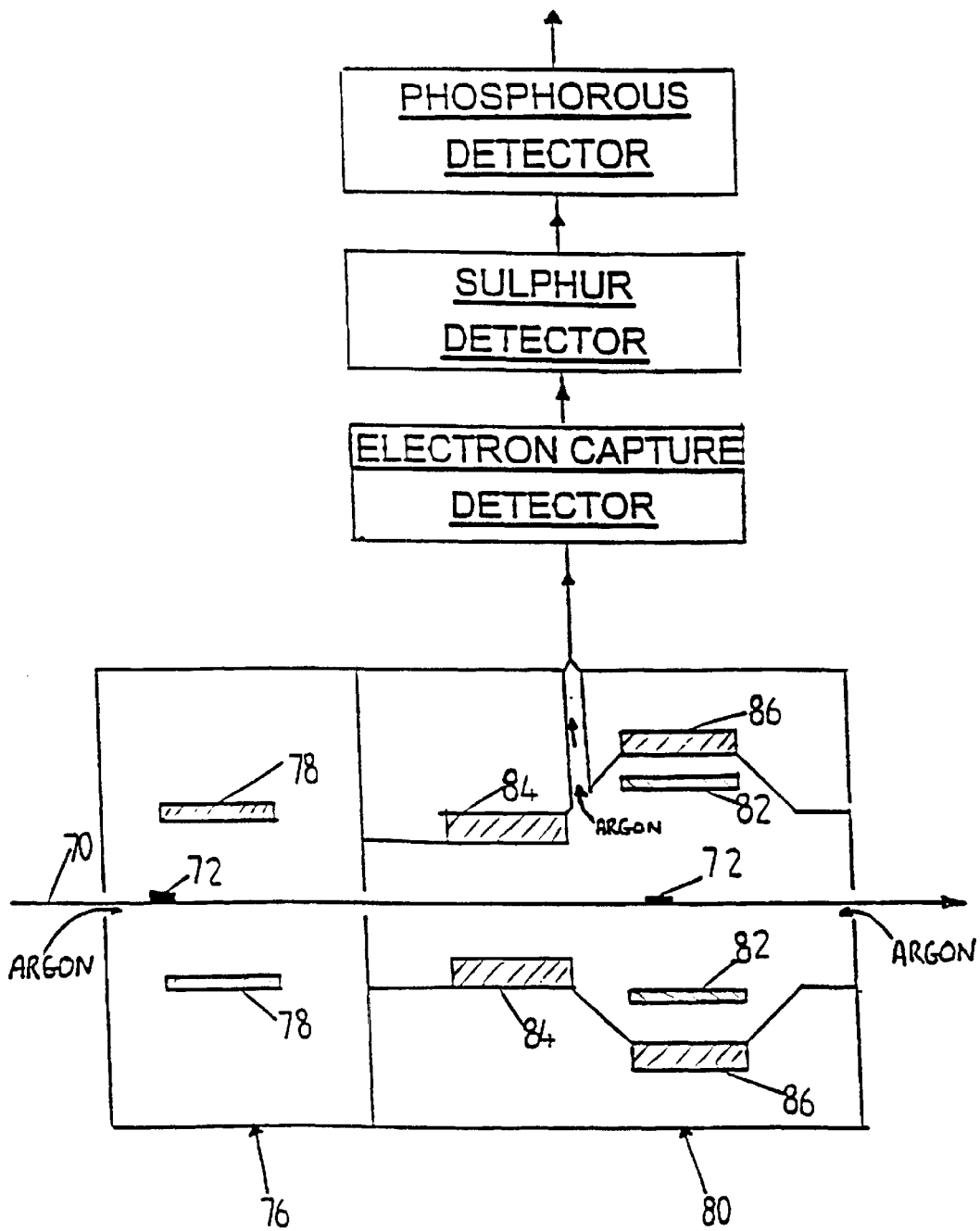
FIG. 4 shows a schematic diagram of an embodiment of the invention.

FIG. 4 shows an alternative embodiment of the invention. Wire 70 onto which sample 72 has been deposited, as previously described, passes into pyrolysis chamber 76 comprising heater 78 which may, if the sample is suitable, be used to pyrolyse sample 72. The wire 70 with the sample 72 is then drawn into the analyser chamber 80. The anlayser chamber 80 comprises an ionising source 82, such as Nickel-63 or Americium, and an anode and cathode 86. Argon is passed through the pyrolyser chamber 76 and analyser chamber 80 in the directions indicated by the arrows. The analysis chamber 80 therefore acts as an argon detector as discussed previously, the presence of a sample being detected by an increase in the curent at the anode 84. Where the sample is not suitable for pyrolysis, or pyrolysis is not desired, the sample 72 is directly bombarded with metastable argon and electrons released are detected by an increase in current at the anode. The Figure also shows argon exiting the analysis chamber 80 and passing to further detectors for more detailed analysis (shown schemtically as) boxes. Pyrolysis will be required if such a multi-detector option is used.

Figure 5:
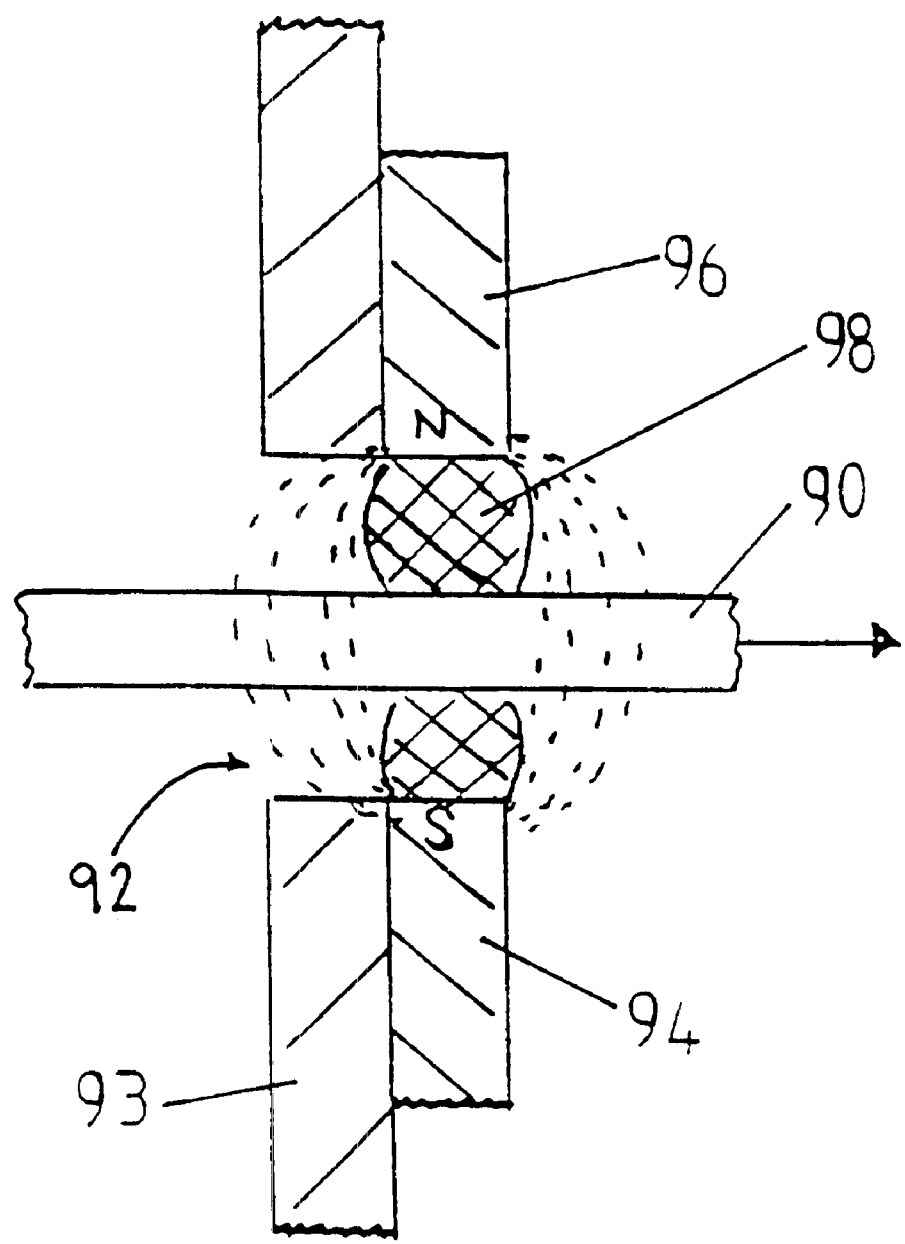
FIG. 5 is a schematic cross-section through a magnetic particle seal according to the invention.

FIG. 5 shows a cross-section through a magnetic particle seal according to the invention. Wire 90 passes through aperture 92 in wall 93. Magnets 94, 96 provide a magnetic field (indicated by dotted lines) between north (N) and south (S) poles of the magnet. The magnetic field keeps a plug 98 of fine magnetisable particles, such as iron powder, around wire 90 and helps to prevent ingress of contaminants through the aperture 92.

Figure 6:
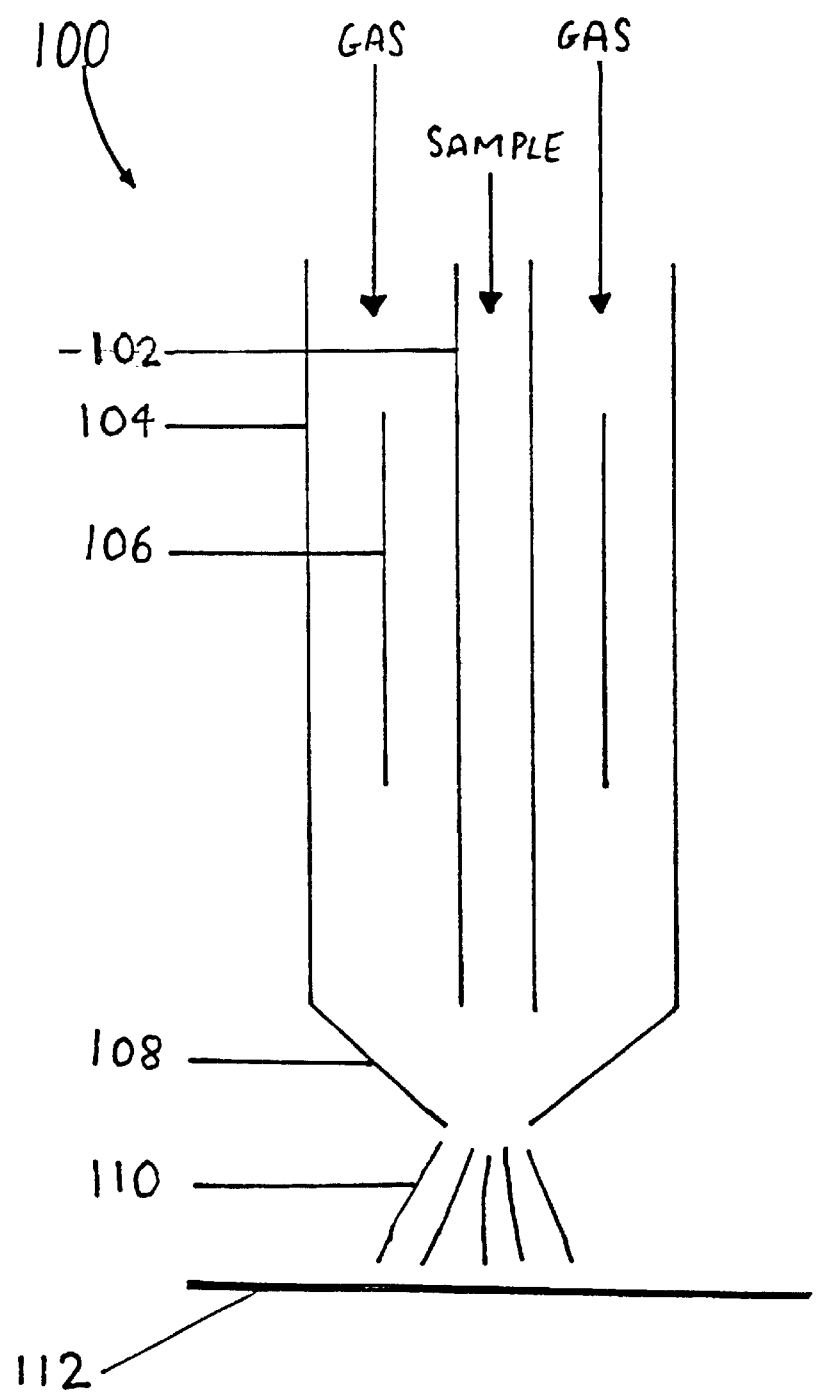
FIG. 6 shows a schematic cross-section of an alternative wetting device for use with the invention.

FIG. 6 shows a nebuliser 100 comprising an inner tube 102 through which the sample to be analysed may be passed. An outer tube 104 around the inner tube 102 channels a supply of gas past heating elements 106 to a nozzle 108 where the sample and gas mix. This sprays the sample 110 onto a conveying means 112, such as wire or tape.

Figure 7:
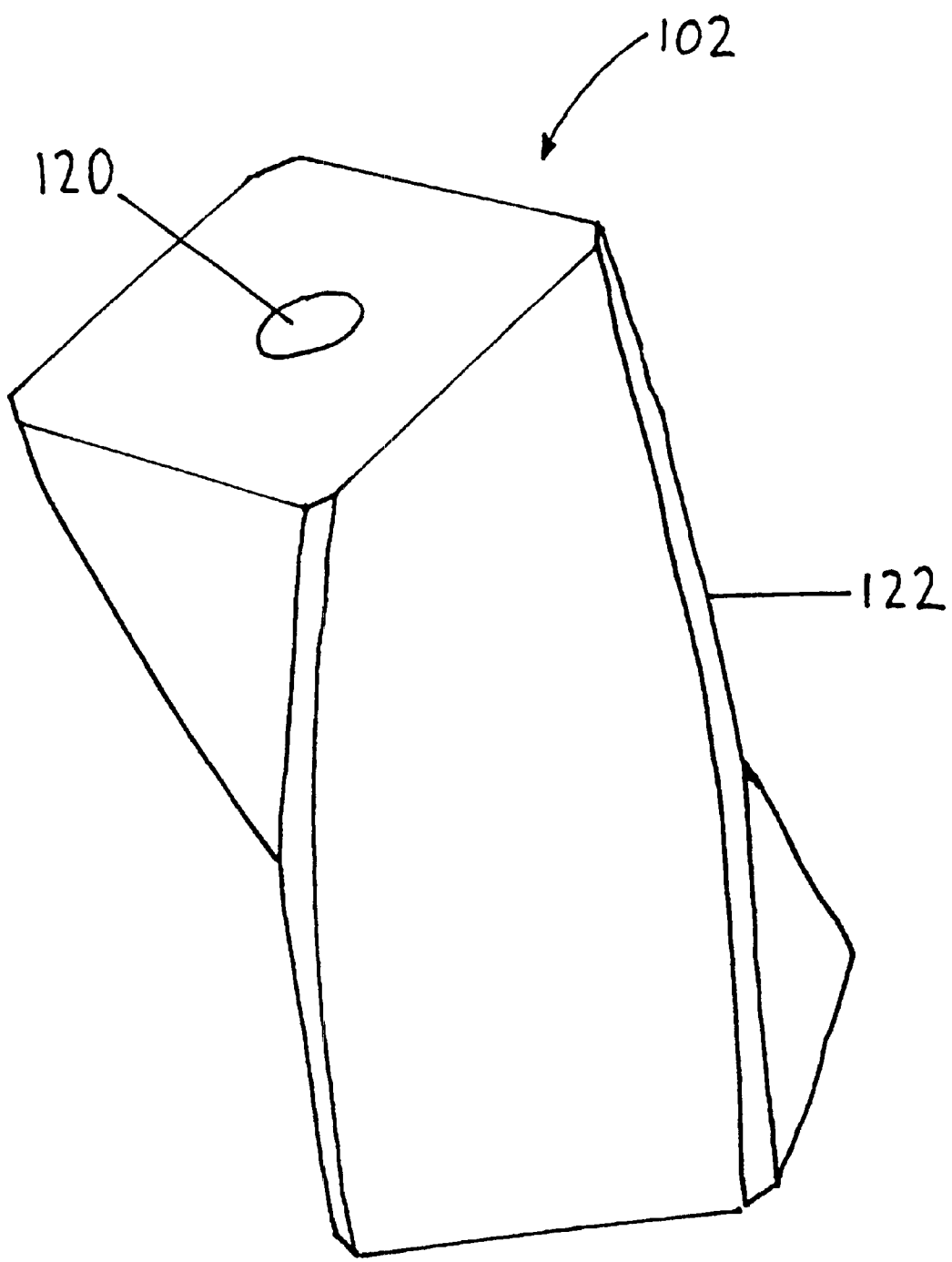
FIG. 7 shows an inner tube for use with the nebuliser of FIG. 6.

FIG. 7 shows a preferred arrangement of inner tube 102 for causing the gas in the outer tube 104 to become turbulent. The inner tube 102, is shown to comprise an inner bore 120, through which the sample is passed, and an outer surface 122 which is twisted into a helix in order to rotate the supply of gas passing through the outer tube 104, prior to mixing with the sample. This improves the spray of the nebuliser.

The inventors have found that the apparatus has a very high sensitivity due to, for example, the use of the argon detector unit. Moreover, unlike some of the earlier detection methods, the present invention is useful for detecting substances which are impossible to detect with the earlier methods. Furthermore the apparatus may be fully automated and made smaller than conventional systems on the market.

What is claimed is:

1. Analytical apparatus comprising:
   (i) a supplier for supplying a sample to be analysed;
   (ii) an analyser for analysing at least one property of the sample to be analysed; and
   (iii) a conveyor operable to convey the sample between the supplier and the analyser wherein the conveyor comprises titanium having an oxidised surface layer which receives the sample.

2. Analytical apparatus according to claim 1, wherein the oxidised surface layer is porous.

3. Analytical apparatus according to claim 1 wherein the conveyor is selected from a belt, a tape, a wire and a disk.

4. Analytical apparatus according to claim 1 comprising an outlet to a supply tube through which the sample is supplied, the supply tube being adjacent the conveyor.

5. Analytical apparatus comprising:
   (i) a supplier for supplying a sample to be analysed;
   (ii) an analyser for analysing at least one property of the sample to be analysed;
   (iii) a conveyor operable to convey the sample between the supplier and the analyser wherein the conveyor comprises titanium having an oxidised surface layer which receives the sample;

an outlet to a supply tube through which the sample is supplied, the supply tube being adjacent the conveyor; and a cone adjacent to the conveyor for receiving surplus sample from the supplier.

6. Analytical apparatus comprising:

(i) a supplier for supplying a sample to be analysed;

(ii) an analyser for analyzing at least one property of the sample to be analysed; and (iii) a conveyor operable to convey the sample between the supplier and the analyzer wherein the conveyor comprises titanium having an oxidized surface layer which receives the sample; and wherein the sample is supplied to the surface of the conveyor by means of a nebuliser.

7. Analytical apparatus according to claim 1, wherein the sample is supplied to the surface of the conveyor by means of a nebuliser.

8. Analytical apparatus according to claim 1, wherein the analyser comprises a pyrolysor.

9. Analytical apparatus according to claim 1, comprising an analyser selected from electron capture detectors, phosphorus or sulphur selective detectors, atomic absorption spectrometers and mass spectrometers.

10. Analytical apparatus according to claim 1 comprising an argon ionisation detector.

11. Analytical apparatus according to claim 9 comprising a pyrolysor in connection with a charge neutraliser, wherein the charge neutralizer is in gaseous connection with an argon ionisation detector.

12. Analytical apparatus according to claim 11, wherein the charge neutraliser comprises an electron capture detector.

13. Analytical apparatus according to claim 1 comprising a seal for an aperture comprising a plurality of magnetisable particles maintained in a sealing position by one or more magnets.

14. Analytical apparatus according to claim 12, wherein the magnetisable particles are iron or iron-coated latex particles.

15. A method of analysing a sample comprising the steps of:

(i) providing a sample to be analysed;

(ii) depositing the sample on a conveyor having a surface layer of oxidized titanium;

(iii) moving the conveyor and the sample thereon to an analyser; and (iv) analysing at least one property of the sample.

16. A method according to claim 15 comprising supplying the sample through a supply tube adjacent the conveyor.

17. A method of analysing a sample comprising the steps of:

(i) providing a sample to be analysed;

(ii) depositing the sample on a conveyor having a surface layer of oxidized titanium;

(iii) moving the conveyor and the sample thereon to an analyser;

(iv) analysing at least one property of the sample; and allowing any surplus sample from said conveyor to be received by a cone adjacent the conveyor.

18. A method according to claim 16 comprising supplying the sample to the conveyor by means of a nebuliser.

19. A method according to claim 15 comprising pyrolysing sample at the analyser.

20. A method according to claim 15 comprising using one or more electron capture detectors, phosphorous or sulphur selective detectors, atomic absorption spectrometers argon ionisation or mass spectrometers.

21. A method according to claim 15 comprising sealing an aperture for the conveyor by means of a plurality of magnetisable particles maintained in a sealing position by one or more magnet.

* * * * *